US012036343B2

(12) United States Patent
Alvarez et al.

(10) Patent No.: US 12,036,343 B2
(45) Date of Patent: Jul. 16, 2024

(54) APPARATUS AND METHODS FOR BIOMIMETIC EXPRESSION OF BREAST MILK

(71) Applicant: Willow Innovations, Inc., Mountain View, CA (US)

(72) Inventors: Jeffery B. Alvarez, Redwood City, CA (US); Polina Segalova, Redwood City, CA (US)

(73) Assignee: Willow Innovations, Inc., Mountain View, CA (US)

( * ) Notice: Subject to any disclaimer, the term of this patent is extended or adjusted under 35 U.S.C. 154(b) by 0 days.

(21) Appl. No.: 17/578,749

(22) Filed: Jan. 19, 2022

(65) Prior Publication Data

US 2022/0133964 A1    May 5, 2022

Related U.S. Application Data

(63) Continuation of application No. 16/580,464, filed on Sep. 24, 2019, now Pat. No. 11,241,521, which is a
(Continued)

(51) Int. Cl.
*A61M 1/06* (2006.01)
*A61M 1/00* (2006.01)

(52) U.S. Cl.
CPC ............ *A61M 1/0697* (2021.05); *A61M 1/06* (2013.01); *A61M 1/064* (2014.02); *A61M 1/066* (2014.02);
(Continued)

(58) Field of Classification Search
CPC ........ A61M 1/06; A61M 1/062; A61M 1/064; A61M 1/066; A61M 1/069; A61M 1/0693;
(Continued)

(56) References Cited

U.S. PATENT DOCUMENTS 6,663,587 B2 * 12/2003 Silver .................... A61M 1/066
119/14.47
9,498,565 B2    11/2016 Nowroozi et al.
(Continued)

FOREIGN PATENT DOCUMENTS

WO    WO 2016033107         3/2016
WO    WO-2016033107 A1 *   3/2016 ............. A61M 1/06

*Primary Examiner* — Robert J Utama
*Assistant Examiner* — Leah J Swanson

(57) ABSTRACT

An apparatus for biomimetic expression of breast milk can comprise a breast interface having an expandable membrane configured to mimic the geometry of an infant's mouth. Various regions of the expandable membrane may be configured to simulate the structure and/or function of various parts of an infant's mouth. The expandable membrane may comprise one or more of a distal sealing region configured to simulate the lips, a superior region configured to simulate the hard palate, an inferior protruding region configured to simulate the gums, an intermediate curved region configured to simulate the tongue, and one or more internal expansion regions configured to simulate the soft palate and the throat. The expandable membrane may have a varying thickness throughout the one or more various regions to enable movement of the regions similar to the movement of the corresponding regions of an infant's mouth during nursing.

16 Claims, 7 Drawing Sheets

Related U.S. Application Data continuation of application No. 15/581,790, filed on Apr. 28, 2017, now Pat. No. 10,434,231.

(60) Provisional application No. 62/329,382, filed on Apr. 29, 2016.

(52) U.S. Cl.
CPC .......... *A61M 1/06935* (2021.05); *A61M 1/75* (2021.05); *A61M 2205/0216* (2013.01); *A61M 2210/1007* (2013.01)

(58) Field of Classification Search
CPC .. A61M 1/06935; A61M 1/0697; A61M 1/75; A61M 2205/0216; A61M 2210/1007
See application file for complete search history.

(56) References Cited

U.S. PATENT DOCUMENTS

| | | | |
|---|---|---|---|
| 11,241,521 B2* | 2/2022 | Alvarez | A61M 1/066 |
| 2006/0111664 A1* | 5/2006 | Samson | A61M 1/82 |
| | | | 604/74 |
| 2007/0060873 A1* | 3/2007 | Hiraoka | A61M 1/82 |
| | | | 604/74 |
| 2016/0015876 A1* | 1/2016 | Tattersfield | A61M 1/062 |
| | | | 604/74 |
| 2016/0287769 A1 | 10/2016 | Makower et al. | |
| 2017/0072118 A1 | 3/2017 | Makower et al. | |
| 2017/0080134 A1 | 3/2017 | Makower et al. | |
| 2017/0173232 A1 | 6/2017 | Chang et al. | |

* cited by examiner

APPARATUS AND METHODS FOR BIOMIMETIC EXPRESSION OF BREAST MILK

CROSS-REFERENCE

The present application is a non-provisional of, and claims the benefit of, U.S. Provisional Patent Application 62/329,382, filed on Apr. 29, 2016, a continuation of U.S. patent application Ser. No. 15/581,790, filed Apr. 28, 2017, and a continuation of U.S. patent application Ser. No. 16/580,464, filed Sep. 24, 2019, the entire contents of which are incorporated herein by reference.

This application is related to the following co-pending provisional and non-provisional patent applications: U.S. patent application Ser. No. 14/221,113, filed on Mar. 20, 2014, now U.S. Pat. No. 9,616,156, U.S. patent application Ser. No. 14/616,557, filed on Feb. 6, 2015, U.S. patent application Ser. No. 14/793,606, filed on Jul. 7, 2015, U.S. patent application Ser. No. 14/793,613, filed on Jul. 7, 2015, U.S. patent application Ser. No. 14/793,617, filed on Jul. 7, 2015, U.S. patent application Ser. No. 14/858,924, filed on Sep. 18, 2015, now U.S. Pat. No. 9,623,160, U.S. patent application Ser. No. 15/094,690, filed on Apr. 8, 2016, U.S. patent application Ser. No. 15/094,704, filed on Apr. 8, 2016, and U.S. patent application Ser. No. 15/349,917, filed on Nov. 11, 2016, the entire contents of which are incorporated herein by reference.

BACKGROUND OF THE INVENTION

1. Field of the Invention

The present invention generally relates to medical and pediatric nutrition devices and methods, and more particularly relates to devices and methods for expression and collection of human breast milk.

Breast pumps are commonly used to collect breast milk in order to allow mothers to continue breastfeeding while apart from their children. Breast pumps typically function by applying a vacuum at the breast to pull on the nipple and the surround tissue while the nipple is constrained within a substantially cylindrical chamber. The nipple can be stretched within the cylinder and the combination of the stretching and the negative pressure within the chamber can result in milk expression.

When a nursing infant expresses milk from the mother's breast, the infant's mouth generally creates a latching suction that pulls the nipple and the surrounding tissue into the mouth. The infant then uses a combination of cyclic vacuum and tongue movements to affect milk movement within the milk ducts of the breast, It would be desirable to provide apparatuses and methods for breast milk expression that simulate the mechanics of how a nursing infant expresses milk from the breast. Such biomimetic expression of breast milk may improve the efficiency of milk expression and increase the comfort of the user during the expression of breast milk.

At least some of these objectives will be satisfied by the devices and methods disclosed below.

SUMMARY OF THE INVENTION

Systems, apparatuses, and methods are disclosed herein for biomimetic expression of breast milk that simulate the mechanics of a nursing infant's mouth during nursing.

In one aspect, an apparatus for biomimetic expression of breast milk from a breast comprises a rigid housing and an expandable membrane coupled to the housing to form a chamber therebetween. The expandable membrane has a distal opening to receive at least a portion the breast therethrough and a proximal opening opposite the distal opening. The expandable membrane is operably coupled to an actuatable assembly configured to alternate between an actuation phase and a resting phase during operation. The expandable membrane comprises an expandable region adjacent the proximal opening, the expandable region configured to expand and move towards the rigid housing during the actuation phase of the actuatable assembly, thereby generating negative pressure at the breast to cause the expression of breast milk from the breast. The expandable membrane further comprises a distal sealing region adjacent the distal opening, the distal sealing region configured to fluidly seal against the breast. The expandable membrane further comprises at least one movable region disposed between the expandable region and the distal sealing region, the at least one movable region configured to move towards the breast during the resting phase to compress the breast.

A thickness of the expandable membrane may vary through different regions of the expandable membrane.

The distal sealing region may comprise an inferior portion having a first wall thickness and a superior portion having a second wall thickness greater than the first wall thickness. The inferior portion of the distal sealing region may be configured to deflect downwards during the actuation phase.

The at least one movable region may comprise an inferior protruding region proximally adjacent an inferior portion of the distal sealing region and protruding radially inwards towards the breast. The inferior protruding region may be configured to compress against a nipple or an areola of the breast during the resting phase. The inferior protruding region may be configured to fold downwards and away from the breast during the actuation phase to allow breast tissue to be pulled proximally into the expandable membrane.

The at least one movable region may comprise an intermediate curved region distally adjacent the expandable region. The intermediate curved region may comprise a central portion disposed between flanking portions, wherein the central portion may have a greater thickness than the flanking portions. The flanking portions may be configured to deflect downwards during the actuation phase and upwards during the resting phase to cause movement of the central portion towards the breast during the resting phase, thereby causing compression of the breast.

The expandable membrane may further comprise a superior region disposed between a superior portion of the distal sealing region and the expandable region. The superior region may comprise a distal portion having a first thickness and a proximal portion having a thickness that gradually decreases from the first thickness to a thickness of the expandable region. The distal portion of the superior region may be configured to compress against the breast when the at least one movable region moves towards the breast during the resting phase. The distal portion of the superior region may comprise a textured internal surface.

The expandable region may be configured to elastically deform during the actuation phase. Alternatively or in combination, the expandable region may comprise one or more pleats or curved portions that allow the region to expand radially outwards during the actuation phase. The expandable region may not directly contact the breast during the expression of breast milk.

The expandable membrane may be operably coupled to the actuatable assembly via a tube coupled to the housing and to the actuatable assembly, wherein the tube and the chamber may be filled with a driving fluid. Actuation of the actuatable assembly may cause movement of the driving fluid into or out of the chamber. The driving fluid may comprise a substantially incompressible fluid.

The expandable membrane may be operably coupled to the actuatable assembly via a mechanical member, wherein actuation of the actuatable assembly causes the mechanical member to mechanically pull the expandable membrane away from the breast. The mechanical member may comprise one or more of a tensile element, an arm, or a lever coupled to the expandable membrane.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Specific embodiments of the disclosed devices and methods will now be described with reference to the drawings. Nothing in this detailed description is intended to imply that any particular component, feature, or step is essential to the invention.

Figure 1:
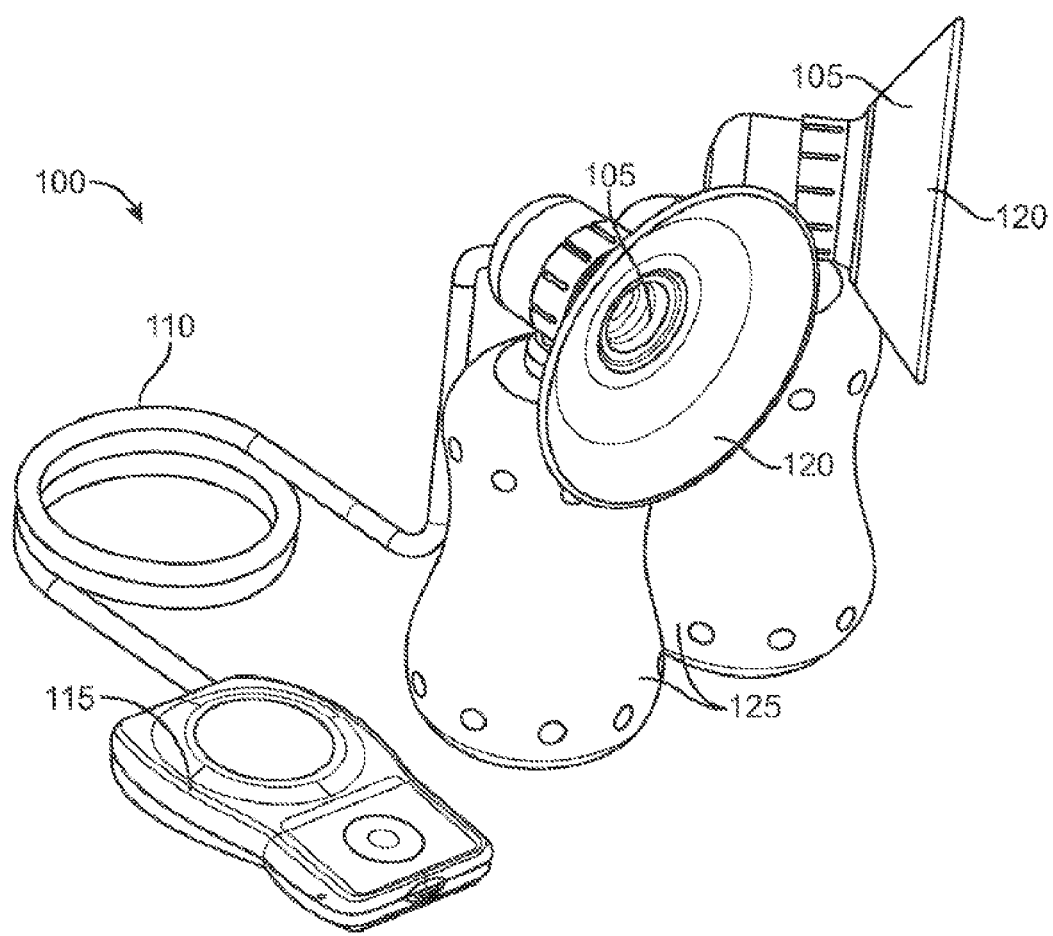
FIG. 1 illustrates an exemplary embodiment of a breast milk expression apparatus or pumping device in accordance with embodiments.

FIG. 1 illustrates an exemplary embodiment of a breast milk expression apparatus or pumping device in accordance with embodiments. Pumping device 100 (also known as an "expression apparatus") includes breast interfaces 105, a tube 110, and a controller 115 operatively coupled to breast interfaces 105 through tube 110. Breast interfaces 105 include resilient and conformable flanges 120, for engaging and creating a fluid seal against the breasts. Each breast interface 105 is fluidly coupled to a collection vessel 125 configured to receive the expressed breast milk. Each breast interface 105 is additionally coupled to one or more controllers 115 that house the power source and drive mechanism for the pumping device 100. For example, the controller 115 may comprise an actuatable assembly for generating negative and/or positive pressure at the breast interface to cause expression of milk from a breast fluidly sealed against the breast interface. Tube 110 may transmit suitable energy inputs, such as mechanical energy generated by an actuatable assembly housed within the controller, from controller 115 to breast interfaces 105. Breast interfaces 105 can then convert the energy inputs into pressure applied against the breasts in a highly efficient manner, resulting in the expression of milk into collection vessels 125. For example, as described in further detail herein, the breast interface may comprise an expandable membrane coupled to a rigid housing, wherein the expandable member expands and contracts in response to actuation of the actuatable assembly apply pressure at the breast and thereby cause expression of milk from the breast.

The controller 115 may further comprise hardware for various functions, such as controlling the pumping device 100, quantifying milk expression, measuring or analyzing data related to characteristics of the expressed milk, and/or communicating with other devices. For example, the controller may be configured to communicate with one or more personal computing devices such as smartphones, tablets, or personal computers, wherein the personal computing device may be configured to provide a user interface for a user to interact with the pumping device.

The device 100 may further comprise one or more sensors configured to track various characteristics of the collected fluid, such as the quantity of the fluid or a composition of the fluid. The one or more sensors may be coupled to one or more portions of the breast interfaces or the collection vessels, or they may be coupled to controller. Power may be provided to the one or more sensors via a connection to the controller 115, or to another source of power. In embodiments in which the one or more sensors are coupled to one or more portions of the breast interfaces 105 or collection vessels 125, the sensors may be further coupled to the controller 115 via one or more communication lines configured to transmit signals between the sensors and the controller.

Figure 2A:
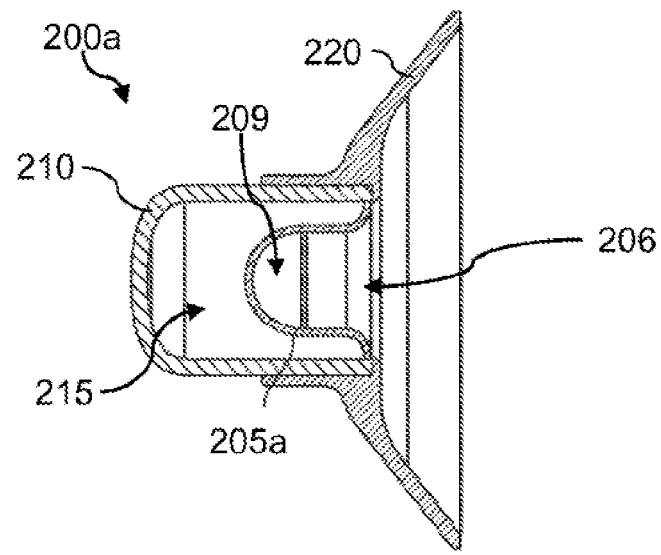
FIGS. 2A and 2B illustrate exemplary embodiments of a breast interface suitable for incorporation with a pumping device as disclosed herein.
Figure 2B:
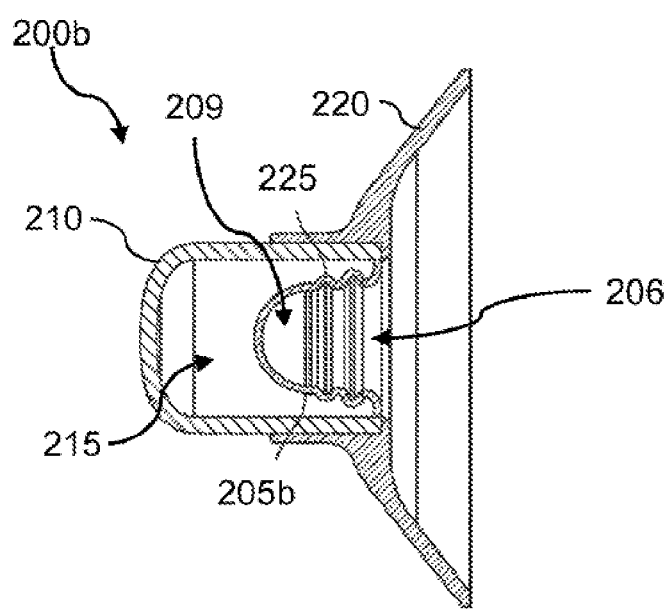

FIGS. 2A and 2B illustrate exemplary embodiments of a breast interface suitable for incorporation with a pumping device as disclosed herein. FIG. 2A shows a breast interface 200a comprising an expandable membrane 205a coupled to a rigid housing 210 to form a reservoir or chamber 215 therebetween. Similarly, FIG. 2B shows a breast interface 200b comprising an expandable membrane 205b coupled to a rigid housing 210 to form a reservoir or chamber 215 therebetween. The expandable membrane 205a or 205b comprises a distal opening 206 through which a nipple and the surrounding breast tissue are received, and an expression area 209 into which the nipple expresses breast milk. The expressed milk exits the expression area through a proximal opening (not shown) of the expandable membrane, and enters a collection reservoir coupled to the breast interface. The breast interface 200a or 200b may further comprise a flange 220 to receive and fluidly seal against a breast.

Optionally, the expandable membrane and the flange may be formed as a single, integrated component, having an expandable portion and a flange portion. The expandable membrane can be configured to expand or contract in response to the actuation of an actuatable assembly operably coupled to the breast interface, thereby causing the volume of the reservoir to decrease or increase, respectively. When the expandable membrane expands, the membrane moves away from the breast received within the breast interface, thereby creating negative pressure at the breast. When the expandable membrane contracts, the membrane moves towards the breast, thereby increasing the pressure at the breast to return the pressure to a baseline level prior to the expansion of the expandable membrane. The reservoir or chamber 215 can therefore provide a sole source of negative pressure for the breast interface, wherein movement of the expandable membrane 205a or 205b towards or away from the breast can generate sufficient negative pressure against the breast to cause the expression of milk, without the aid of additional pressure sources such as air suction applied directly to the nipple.

The expandable membrane 205a shown in FIG. 2A comprises a flexible or elastic material allowing the membrane to elastically deform in response to the actuation of the pumping mechanism. For example, the expandable membrane 205a may comprise one or more of silicone, polyether block amides such as PEBAX, or polychloroprenes such as neoprene, and can have a specified thickness and durometer. The expandable membrane 205b shown in FIG. 2B comprises a membrane having one or more corrugated features 225 (such as pleats) that allow expansion and contraction of the membrane. The expandable membrane 205b may comprise an elastically deformable material as described in reference to expandable membrane 205a of FIG. 2A. Alternatively, the expandable membrane 205b may be fabricated from a substantially rigid material, such as stainless steel, nitinol, high durometer polymer, or high durometer elastomer. In these embodiments, the one or more corrugated features can provide stress and/or strain distribution to enable the substantial deformation of the expandable membrane without surpassing the yield point of the material. The amount of deformation of the expandable membrane can be controlled by many factors, (e.g., wall thickness, durometer, surface area) and can be optimized based on the pumping device (e.g., pump power, vacuum requirements).

In some embodiments, the expandable membrane is operably coupled with the actuatable assembly via a fluid. For example, chamber 215 comprises a fluid reservoir filled with a fluid, and the actuatable assembly of the pumping device comprises a hydraulic pumping mechanism fluidly coupled with the reservoir. Negative pressure can be generated at the breast interface when the fluid is displaced from reservoir by actuation of the actuatable assembly. The driving fluid may comprise any suitable fluid for transferring sufficient pressure from the actuatable assembly to the expandable membrane to cause the expression of milk from the breast. In many embodiments, the driving fluid may be a substantially incompressible fluid, such as water or oil. Suitable incompressible fluids for hydraulic systems are known to those of skill in the art. In some embodiments, the expandable membrane may be operably coupled with the actuatable assembly via a mechanical member. For example, the mechanical member may comprise a tensile element (e.g., cable, coil, spring, etc.), an arm, or a lever coupled to the expandable membrane, wherein actuation of the actuatable assembly causes the mechanical member to mechanically pull the expandable member away from the breast received within the breast interface, thereby generating negative pressure at the breast.

At the beginning of a breast milk expression session, wherein the nipple and surrounding breast tissue is received through the distal opening of the expandable membrane, the chamber or reservoir between the membrane and the housing of the breast interface may be at atmospheric pressure $P_{ATM}$. To begin expressing milk, the actuatable assembly may be prompted to begin a pumping session, wherein the actuatable assembly repeatedly alternates between an actuation phase and a resting phase throughout a pumping session. During the actuation phase, the expandable membrane expands and moves away from the breast tissue fluidly sealed against the membrane, causing the pressure at the chamber to decrease to a pre-determined maximum negative pressure $-P_{MAX}$. During the resting phase, the expandable membrane contracts and moves towards the breast tissue, causing the pressure at the chamber to increase from the maximum negative pressure $-P_{MAX}$ to either atmospheric pressure $P_{ATM}$ or a pre-determined minimum negative pressure $-P_{MIN}$. The cyclical actuation of the actuatable assembly can thus mimic the sucking cycles of an infant during a nursing session. During each of the actuation phase and the resting phase, the chamber may be held at the maximum and minimum vacuum pressures, respectively, for a pre-determined length of time to model the nursing cycle of an infant.

To better simulate the mechanism of action of an infant's mouth during nursing, the breast interface as described herein may comprise an expandable membrane having a biomimetic geometry, specifically designed to emulate the geometry of an infant's mouth. Such a membrane may be configured expand and contract in response to actuation of an actuatable assembly to apply negative pressure at the breast, as described herein. In addition, the membrane may comprise various features configured to mimic the functions of various portions of the infant's mouth during nursing.

Figure 3A:
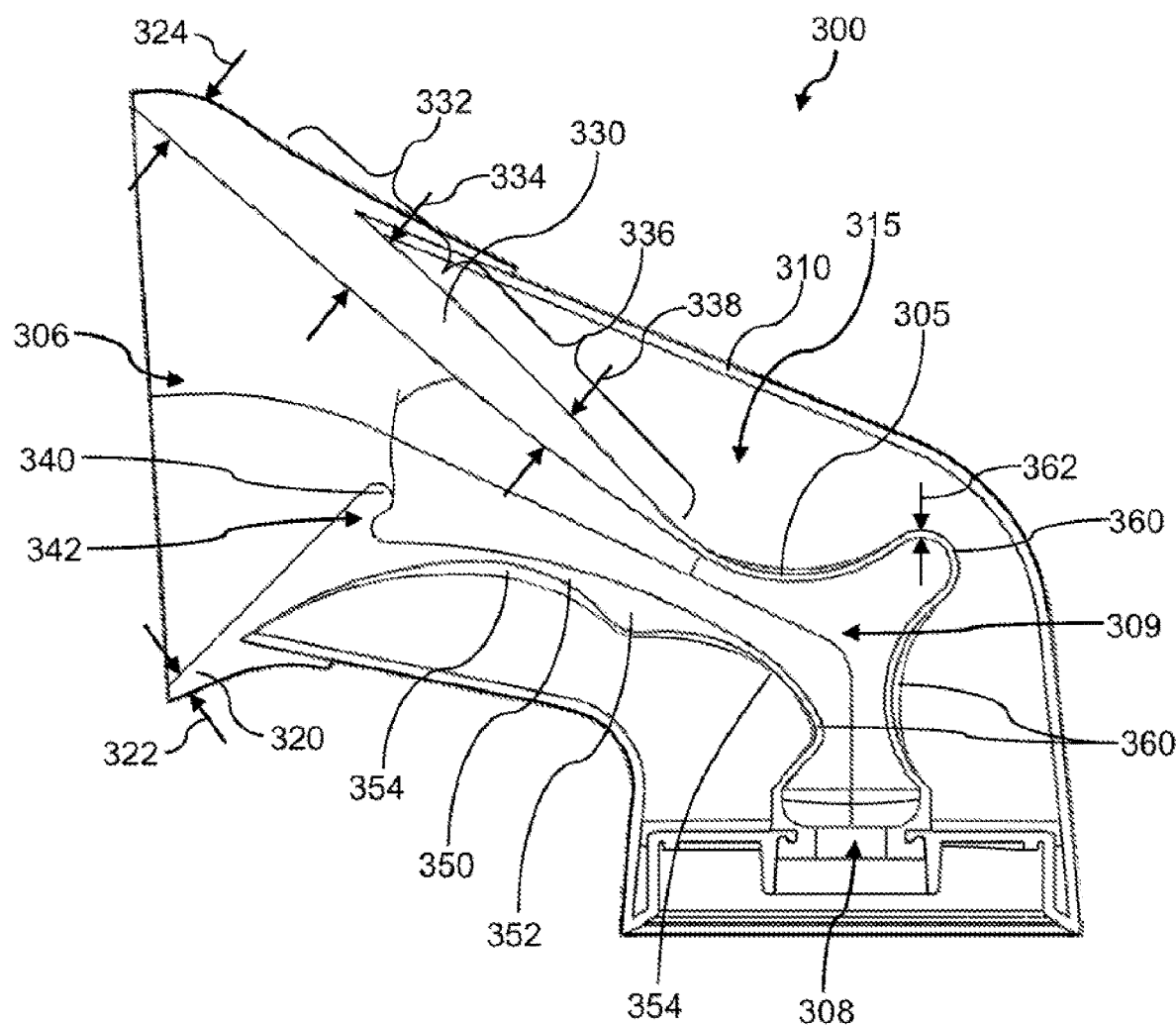
FIG. 3A is a sectional view of an exemplary embodiment of a breast interface comprising an expandable membrane having biomimetic geometry.
Figure 3B:
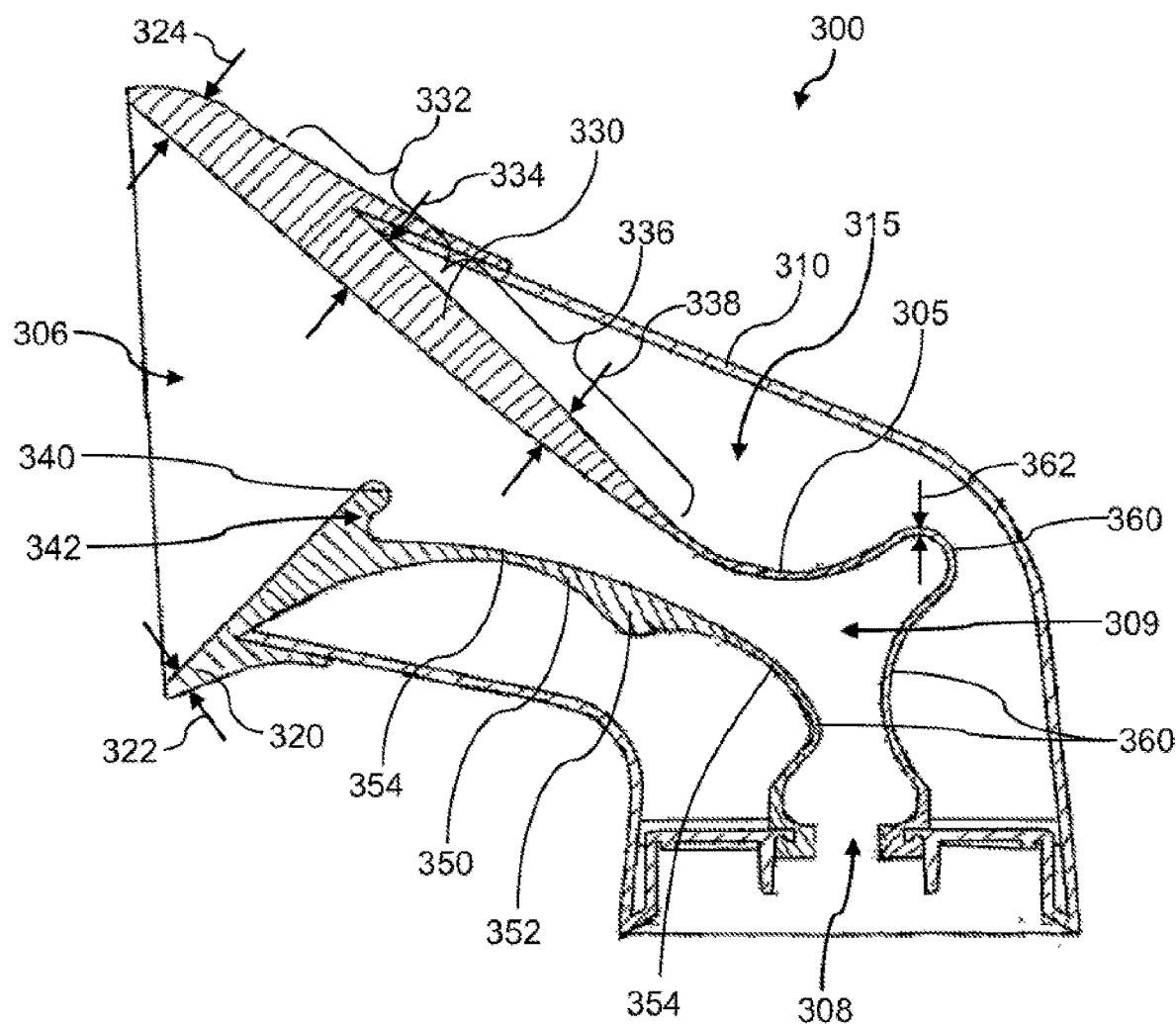
FIG. 3B is a 2D cross-section of the breast interface of FIG. 3B.

FIGS. 3A and 3B illustrate an exemplary embodiment of a breast interface 300 comprising an expandable membrane 305 having biomimetic geometry. FIG. 3A is a sectional view of the breast interface 300, and FIG. 3B is a 2D cross-section of the breast interface 300. The expandable membrane 305 may be coupled to a rigid housing 310, thereby forming a chamber or reservoir 315 between the membrane and the housing. The expandable membrane may comprise a distal opening 306 to receive the nipple and the surrounding breast tissue, a proximal opening 308 to couple to a collection reservoir (not shown), and an expression area 309 into which the nipple expresses milk.

As described herein, the expandable membrane may be operably coupled with an actuatable assembly to affect expansion and contraction of the expandable membrane and thereby cause the expression of milk from a nipple received within the expandable membrane through the distal opening. For example, the chamber 315 may be filled with a fluid, and the housing may comprise a tubing outlet (not shown) connected to tubing also filled with the fluid. The actuatable assembly may be operably coupled with the tubing and configured to affect movement of the fluid within the tubing towards or away from the breast interface. The movement of the fluid within the tubing can in turn cause movement of the fluid into or out of the chamber 315, affecting a corresponding contraction or expansion of the expandable member to apply pressure at the breast interface. Movement of the fluid out of the chamber, causing the corresponding expansion of the expandable membrane and hence movement of the membrane away from the breast captured within the membrane, can apply negative pressure at the breast, which can cause milk be expressed from the nipple. Movement of the fluid into the chamber, causing the contraction of the expandable membrane and hence movement of the membrane toward the breast, can relieve at least a portion of the negative pressure applied at the breast due to the expansion of the membrane. The fluid may be a substantially incompressible fluid such as water or oil.

The geometry of the expandable membrane 305 may be configured to mimic the geometry of an infant's mouth. Various regions of the expandable membrane may be configured to simulate the structure and/or function of various parts of an infant's mouth. For example, as shown, the expandable membrane may comprise one or more of a distal sealing region 320, a superior region 330, an inferior protruding region 340, an intermediate curved region 350, and one or more internal expansion regions 360. The distal sealing region 320 can form a fluid seal against the breast received within the breast interface 300, similar in function to the lips of an infant. The superior region 330 may simulate the hard palate of an infant's mouth, which directs the nipple and the surrounding breast tissue toward the throat. The inferior protruding region 340 may simulate the gums of an infant's mouth, and can provide pinching of the captured breast tissue captured upon reduction of vacuum at the breast interface. The curved region 350 can simulate the tongue of an infant. The expansion regions 360 can simulate the throat and the soft palate of an infant's mouth.

The expandable membrane 305 may have a varying thickness throughout the one or more various regions. When negative pressure is applied at the breast interface, the localized thickening or thinning of each region can enable movement of the region similar to the movement of a corresponding region of an infant's mouth during nursing.

The distal sealing region 320, which fluidly seals against the nipple and the surrounding breast tissue, may have an inferior nominal wall thickness 322 on the inferior portion and a superior wall thickness 324 on the superior portion, wherein the superior thickness 324 is greater than the inferior thickness 322. Therefore, the superior portion of the sealing region can be relatively rigid, while the inferior portion can be relatively flexible. When the actuatable assembly coupled to the breast interface is actuated and negative pressure is applied at the breast, the thicker, more rigid superior portion can push against the top portion of the breast, while the thinner, more flexible inferior portion can be deflected to allow the lower portion of the breast to be pulled further inwards toward the expression area 309.

The superior region 330 may comprise a texture or ridged interior surface facing the breast, which can direct the nipple inwards towards the expression area 309 when negative pressure is applied at the breast. The distal portion 332 of the superior region can comprise a distal thickness 334 sufficient to provide structural rigidity to the region, such that the region does not deflect significantly when the nipple and the surrounding breast tissue are compressed against the region. When negative pressure is applied at the breast, the nipple may be pushed upwards against the superior region via movement of the intermediate curved region, as described herein, such that the nipple is compressed between the super rigid region and the intermediate curved region. The proximal portion 336 of the superior region can comprise a gradually decreasing thickness that tapers into the expansion region 360. For example, a proximal thickness 338 of the region within the proximal portion 336 may be smaller than the distal thickness 334. Thus, the superior region 330 gradually translates into the flexible expandable region 360.

The expandable region 360 is disposed near the proximal opening 308 of the expandable membrane, and is configured to expand radially outwards, generally away from the nipple captured within the expandable membrane, when negative pressure is applied at the breast interface. For example, the reservoir 315 may be filled with a fluid, and actuation of an actuatable assembly fluidly coupled with the reservoir may cause movement of fluid out of the reservoir 315, in turn causing the expandable region to be pulled towards the rigid housing 310. The expansion of the expandable region applies negative pressure at the breast tissue that is received through the distal opening 306 and fluidly sealed against the expandable membrane. The expandable region can comprise a thickness 362 that allows the region to elastically deform in response to the pressure applied at the expandable region. Additionally, the expandable region may comprise one or more pleats or curved portions that allow the region to expand radially outwards towards the rigid housing. In some embodiments, the expandable region does not directly contact the nipple or the surrounding breast tissue, similarly to the throat and soft palate of the infant during nursing.

The intermediate curved region 350 comprises a thicker central portion 352 disposed between thinner flanking portions 354. During the pumping cycle, the thinner flanking portions can deflect, thereby allowing the thicker central portion to move up and down towards and away from the nipple. The breast tissue can be thus compressed between the thicker central portion of the curved region and the superior region 330. In preferred embodiments, the intermediate curved region is configured to compress the breast tissue during the resting phase of the pumping session, or as the expandable membrane is contracting and moving back towards the breast. During the resting phase, the chamber 315 is returning to either atmospheric pressure or minimum vacuum pressure (e.g., during the part of the pump cycle wherein fluid volume in the reservoir 315 is increasing). The intermediate curved region can thus function similarly to a tongue of an infant, creating localized compression of the breast tissue inbetween sucking cycles. As the actuatable assembly transitions from the resting phase to the actuation phase, the thinner flanking portions can deflect to move the thicker central portion downwards and away from the breast tissue, thereby helping create negative pressure at the breast.

The inferior protruding region 340 may be disposed centrally over the inferior portion of the distal opening 306 into the expression area 309. The inferior protruding region can fold or unfold about an axis 342 to create localized compression at the breast tissue near the nipple. During the actuation phase, as pressure at the chamber 315 decreases to the maximum negative pressure and the breast tissue is pulled further into the expandable membrane towards the expression area 309, the inferior protruding region can move downwards and away from the breast tissue, "folding" about the axis 342. During the resting phase, as the pressure in the chamber increases to atmospheric or the minimum negative pressure and the breast tissue retreats or moves away from the expression area 309, the inferior protruding region can move upwards and into the breast tissue, "unfolding" about the axis 342. As the inferior protruding region moves upwards and into the breast tissue, localized compression is created at the breast tissue near the nipple, similarly to the gums of an infant's mouth.

Figure 4A:
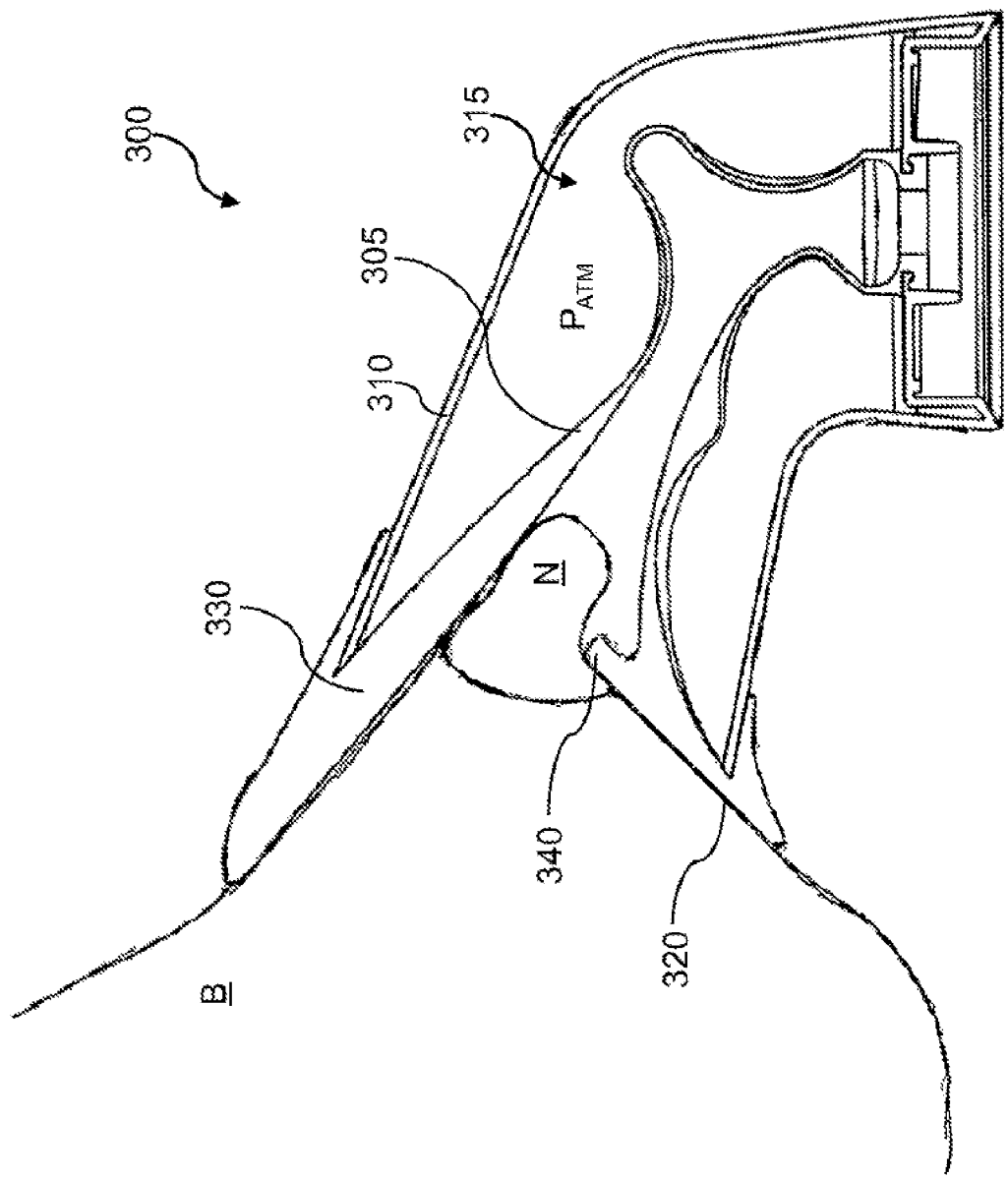
FIG. 4A illustrates the position of a breast at the beginning of a breast milk expression session using the breast interface of FIGS. 3A and 3B.

FIG. 4A illustrates the position of a breast B at the beginning of a breast milk expression session using the breast interface 300 of FIGS. 3A and 3B. The breast B is received through the distal opening of the expandable membrane 305 with the nipple N resting just past the inferior protruding region 340 (the "gums" element) and mid-way through the superior region 330. The chamber 315 is at atmospheric pressure $P_{ATM}$.

Figure 4B:
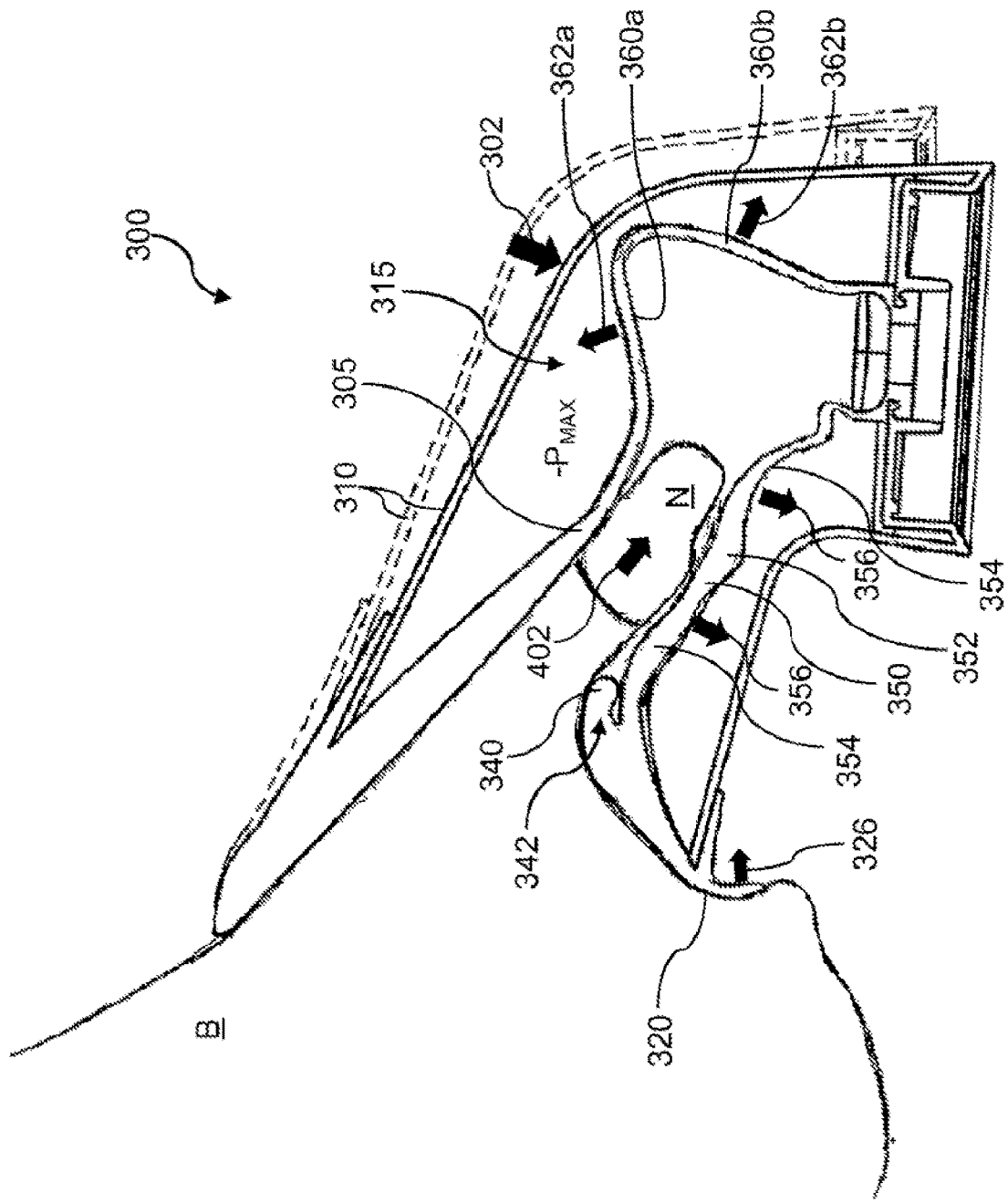
FIG. 4B illustrates the interaction between the breast and the breast interface of FIGS. 3A and 3B at maximum vacuum pressure.

FIG. 4B illustrates the interaction between the breast B and the breast interface 300 at maximum vacuum pressure. As the chamber 315 reaches maximum negative pressure $-P_{MAX}$ via actuation of the actuatable assembly operably coupled with the expandable membrane 305, the expandable regions 360a and 360b expand and move in directions 362a and 362b, respectively. In addition, the thinner flanking portions 354 of the intermediate curved region 350 deflect downwards in the direction 356, such that the thicker central portion 352 also moves downwards and away from the nipple N. The movement of the expandable regions and the intermediate curved region towards the housing 310 and generally away from the breast B creates negative pressure at the chamber 315, which is transferred to the breast via the expandable membrane. The negative pressure causes the nipple to be pulled further into the expandable membrane in the direction 402. Accordingly, as the breast tissue is pulled further into the expandable membrane, the breast tissue applies a reaction force 326 to the relatively flexible inferior portion of the distal sealing region 320, which in turn causes the inferior portion of the distal sealing region to deflect and pivot slightly downwards as shown. The deflection of the inferior portion of the sealing region allows more of the lower breast tissue to be pulled into the expandable membrane. As the nipple N is pulled over the inferior protruding region 340, the insertion force of the breast tissue causes the inferior protruding region to fold downwards about its axis 342 as shown, such that the nipple can rest over the intermediate curved region 350. In addition, the folding of the inferior protruding region can cause the breast interface 300 to pivot slightly with respect to the breast in the direction 302.

Figure 4C:
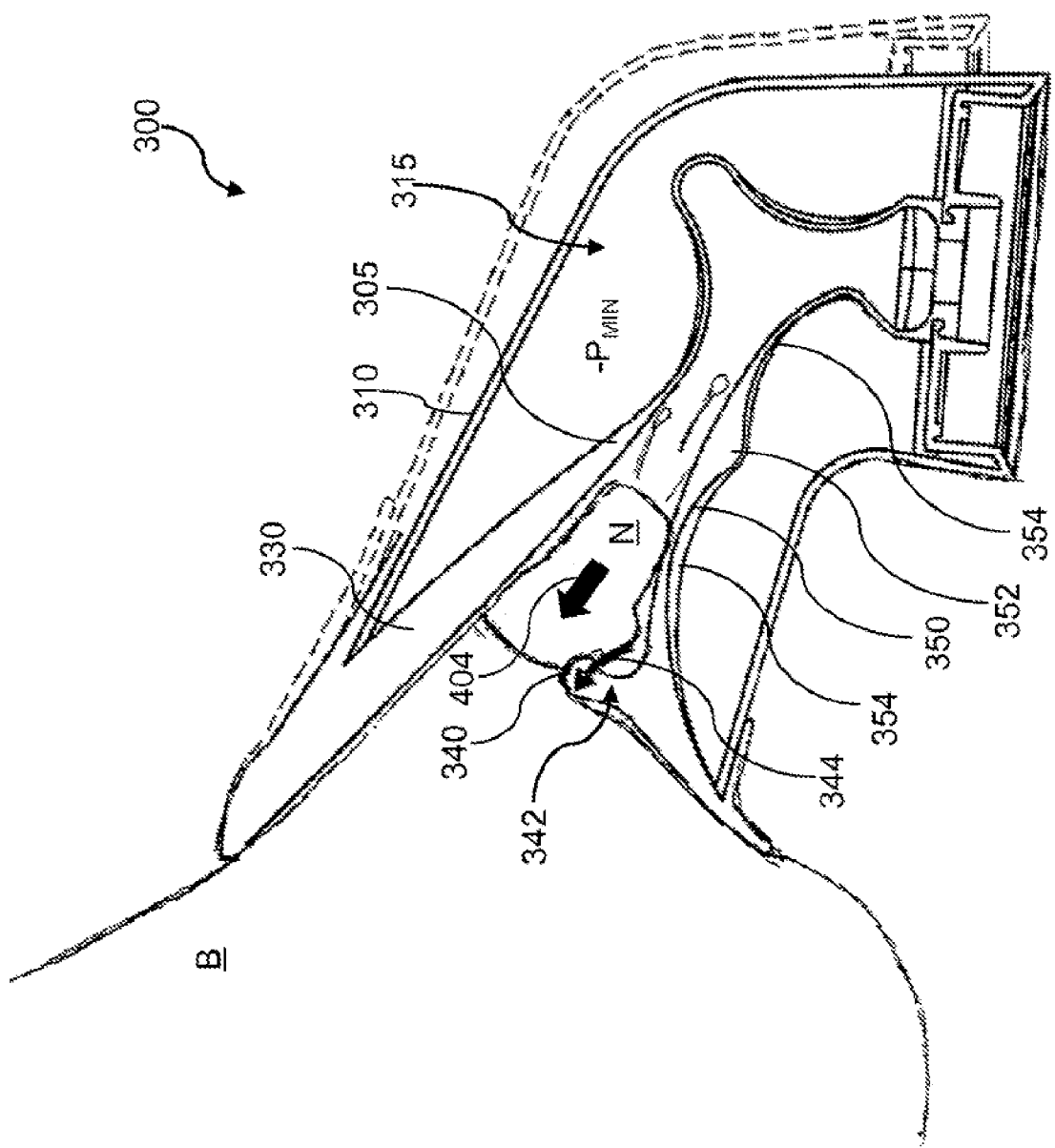
FIG. 4C illustrates the interaction between the breast and the breast interface of FIGS. 3A and 3B at minimum vacuum pressure.

FIG. 4C illustrates the interaction between the breast B and the breast interface 300 at minimum vacuum pressure. As described herein, as the actuatable assembly transitions from the actuation phase to the resting phase to release at least a portion of the negative pressure generated during the actuation phase (e.g., by returning fluid to the chamber 315, causing the expandable membrane 305 to contract), the chamber 315 returns to atmospheric pressure or a pre-determined minimum negative pressure $-P_{MIN}$. The breast interface may be held at the minimum negative pressure $-P_{MIN}$ for a pre-determined length of time. As negative pressure in the chamber 315 is at least partially released, the breast tissue retreats in the direction 404, relieving the insertion force exerted onto the inferior protruding region 340 during the actuation phase. Accordingly, the inferior protruding region 340 unfolds in the direction 344 about the axis 342, digging into the breast tissue and causing localized compression on the areola and the nipple. As described herein, the thicker central portion 352 of the intermediate curved region 350 can also move upwards during the transition from the actuation phase to the resting phase, compressing the nipple against the upper region. Compression with the inferior protruding region and/or the intermediate curved region can compress the milk ducts of the breast to cause the milk within the milk ducts to flow out through the nipple.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for biomimetic expression of breast milk from a breast, the apparatus comprising:
   a housing; and
   a membrane coupled to the housing, the membrane having a distal opening to receive at least a portion of the breast therethrough and a proximal opening opposite the distal opening, the distal opening including an inferior portion that is configured to be located on an underside of the breast and a superior portion that is configured to be located on an upper surface of the breast,
   wherein the membrane is operably coupled to an actuatable assembly configured to alternate between a first phase and a second phase during operation, and
   wherein the membrane comprises at least one movable region disposed between the distal opening and the proximal opening and configured to be responsive to a transition from the first phase to the second phase, the at least one movable region including a portion that folds against the moveable region of the membrane during biomimetic expression of breast milk from a breast and is configured to simulate a gum element and provide pinching of the breast, the portion that folds against the moveable region of the membrane being limited to the inferior portion of the distal opening.

2. An apparatus as in claim 1, wherein a thickness of the membrane varies through different regions of the membrane.

3. An apparatus as in claim 1, wherein the membrane comprises a distal sealing region adjacent the distal opening, the distal sealing region comprises an inferior portion configured to be located on an underside of the breast and having a first wall thickness and a superior portion configured to be located on an upper surface of the breast and having a second wall thickness greater than the first wall thickness.

4. An apparatus as in claim 3, wherein the inferior portion of the distal sealing region configured to be located on an underside of the breast is configured to deflect downwards during the first phase.

5. An apparatus as in claim 1, wherein the membrane comprises a distal sealing region adjacent the distal opening and wherein the portion that folds against the moveable region of the membrane defines an inferior protruding region proximally adjacent an inferior portion of the distal sealing region configured to be located on an underside of the breast and protruding radially inwards towards the breast.

6. An apparatus as in claim 5, wherein the inferior protruding region is configured to compress against a nipple or an areola of the breast during the second phase.

7. An apparatus as in claim 5, wherein the inferior protruding region is configured to fold downwards and away from the breast during the first phase to allow breast tissue to be pulled proximally into the membrane.

8. An apparatus as in claim 1, further comprising an expandable region, wherein the at least one movable region comprises an intermediate curved region distally adjacent the expandable region, the intermediate curved region comprising a central portion disposed between flanking portions, the central portion having a greater thickness than the flanking portions, and the flanking portions configured to deflect downwards during the first phase and upwards during the second phase to cause movement of the central portion towards the breast during the second phase, thereby causing compression of the breast.

9. An apparatus as in claim 1, further comprising an expandable region, wherein the membrane further comprises a superior region disposed between a superior portion of a distal sealing region configured to be located on an upper surface of the breast and the expandable region, the superior region comprising a distal portion having a first thickness and a proximal portion having a thickness that gradually decreases from the first thickness to a thickness of the expandable region.

10. An apparatus as in claim 9, wherein the distal portion of the superior region is configured to compress against the breast when the movable region moves towards the breast during the second phase.

11. An apparatus as in claim 10, wherein the distal portion of the superior region comprises a textured internal surface.

12. An apparatus as in claim 1, further comprising an expandable region, wherein the expandable region is configured to elastically deform during the first phase.

13. An apparatus as in claim 1, further comprising an expandable region, wherein the membrane comprises one or more pleats or curved portions that allow the expandable region to expand radially outwards during the first phase.

14. An apparatus as in claim 1, wherein a portion of the membrane does not directly contact the breast during the expression of breast milk.

15. An apparatus as in claim 1, wherein the membrane forms a chamber with the housing and the membrane is operably coupled to the actuatable assembly via a tube coupled to the housing and to the actuatable assembly, wherein the tube and the chamber are filled with a driving fluid, and wherein actuation of the actuatable assembly causes movement of the driving fluid into or out of the chamber.

16. An apparatus as in claim 15, wherein the driving fluid comprises a substantially incompressible fluid.

* * * * *